US012053212B2

(12) United States Patent
Afshar et al.

(10) Patent No.: US 12,053,212 B2
(45) Date of Patent: Aug. 6, 2024

(54) IMPLANT ASSEMBLY INCLUDING SCREW LOCKING MECHANISM

(71) Applicant: FloSpine, LLC, Boca Raton, FL (US)

(72) Inventors: John Afshar, Jupiter, FL (US); John R. Robinson, Port St Lucie, FL (US); Cheng L. Soo, Oklahoma City, OK (US); Brett Schlifka, Boynton Beach, FL (US); Thomas Fellman, Lake Worth, FL (US); James Spitler, Winter Garden, FL (US); James Szalas, Ft. Lauderdale, FL (US); Peter Harris, Boca Raton, FL (US)

(73) Assignee: FloSpine, LLC, Boca Raton, FL (US)

( * ) Notice: Subject to any disclaimer, the term of this patent is extended or adjusted under 35 U.S.C. 154(b) by 537 days.

(21) Appl. No.: 17/306,867

(22) Filed: May 3, 2021

(65) Prior Publication Data

US 2021/0338289 A1 Nov. 4, 2021

Related U.S. Application Data

(60) Provisional application No. 63/062,480, filed on Aug. 7, 2020, provisional application No. 63/018,729, filed on May 1, 2020.

(51) Int. Cl.
*A61B 17/70* (2006.01)
*A61B 17/00* (2006.01)

(52) U.S. Cl.
CPC ...... *A61B 17/7058* (2013.01); *A61B 17/7082* (2013.01); *A61B 2017/00455* (2013.01)

(58) Field of Classification Search
CPC ............ A61B 17/7058; A61B 17/7082; A61B 2017/00455
See application file for complete search history.

(56) References Cited

U.S. PATENT DOCUMENTS

| | | | |
|---|---|---|---|
| 6,558,423 B1 | 5/2003 | Michelson | |
| 6,890,335 B2 | 5/2005 | Grabowski et al. | |
| 8,652,182 B1* | 2/2014 | Walker | A61B 17/8042 606/295 |
| 9,248,027 B2 | 2/2016 | Dunworth et al. | |
| 10,166,115 B2 | 1/2019 | Kana et al. | |
| 10,751,185 B2 | 8/2020 | Dawson et al. | |
| 2005/0187552 A1* | 8/2005 | Michelson | A61B 17/7058 606/295 |
| 2016/0310180 A1* | 10/2016 | Prybis | A61B 17/808 |

* cited by examiner

*Primary Examiner* — Nicholas J Plionis
(74) *Attorney, Agent, or Firm* — David Meibos; Maywood IP Law

(57) ABSTRACT

An implant assembly may include a screw with a head having a head feature and an implant. The implant may be securable to a bone of a patient with the screw. The implant may include a bone plate, a rotatable structure having a top surface and a bottom surface. The bottom surface may include a lock feature. The lock feature may engage the head feature when the rotatable structure is in a locked orientation and disengage the head feature when the rotatable structure is in an unlocked orientation. The rotatable structure may couple to the bone plate such that the rotatable structure is rotatable between the locked orientation and the unlocked orientation. The head feature may be one of a ridge and a radial groove and the lock feature may be the other one of the ridge and the radial groove.

22 Claims, 11 Drawing Sheets

IMPLANT ASSEMBLY INCLUDING SCREW LOCKING MECHANISM

CROSS-REFERENCE TO RELATED APPLICATIONS

The present application claims the benefit of U.S. Provisional Patent Application Ser. No. 63/062,480, entitled CERVICAL PLATE INCLUDING SCREW LOCKING MECHANISM UTILIZING RADIAL GROOVES, which was filed on Aug. 7, 2020, which is incorporated by reference as though set forth herein in its entirety. The present application also claims the benefit of U.S. Provisional Patent Application Ser. No. 63/018,729, entitled CERVICAL PLATE INCLUDING SCREW LOCKING MECHANISM UTILIZING RADIAL GROOVES, which was filed on May 1, 2020, which is incorporated by reference as though set forth herein in its entirety.

TECHNICAL FIELD

The present disclosure relates to implant assemblies. More specifically, the present disclosure relates to improved implant assemblies that include locking mechanisms for screws, or other fasteners, that secure an implant to bone of a patient.

BACKGROUND

Bone implants and bone fixation procedures and implants have been used to secure two bones or bone parts or to fix one bone relative to other bones. For example in spinal fixation intervertebral implants can be used to secure, or fixate, two or more vertebrae through minimally invasive or invasive spinal surgery. Conventional implant assemblies can include screws that engage bone and secure the implant to the bone. However, over time the bone screws can become loose, or threads of screws can strip from the bone. This stripping and loosing can cause the screw to back out of a screw hole or rotate and loosen with the screw hole. Consequently, blocks or locks can be used to retain the screw within a screw opening of an implant. Unfortunately, existing blocks or locks do not adequately retain screws within an implant. Accordingly, a need exists for improved implant assemblies.

SUMMARY

The various apparatus, devices, systems, and/or methods of the present disclosure have been developed in response to the present state of the art, and in particular, in response to the problems and needs in the art that have not yet been fully solved by currently available implants. The apparatus, devices, systems, and/or methods of the present disclosure may provide implant assemblies that remedy shortcomings of prior art implants.

To achieve the foregoing, and in accordance with the disclosure as embodied and broadly described herein, an implant assembly may be provided. One general aspect of the implant assembly can include a screw that may also include a head which may include a head feature which may include one of a ridge and a radial groove. The implant assembly may also include an implant securable to a bone of a patient with the screw. The implant may include: a bone plate that may have a screw opening sized to receive the screw. The implant may also include a rotatable structure coupled to the bone plate such that the rotatable structure is rotatable between a locked orientation and an unlocked orientation, the rotatable structure may include: a top surface; a bottom surface that may include a lock feature that may include the other of the ridge and the radial groove. The implant assembly may also include where the lock feature is positioned such that: with the rotatable structure in the locked orientation, the lock feature engages the head feature, thereby restricting rotation of the screw within the screw opening; and with the rotatable structure in the unlocked orientation, the lock feature disengages from the head feature, thereby permitting rotation of the screw within the screw opening.

Implementations may include one or more of the following features. The implant assembly where the lock feature may include a plurality of radial grooves and the head feature may include a plurality of ridges, the plurality of radial grooves adapted to engage the plurality of ridges. The implant assembly may include a rotation limiter adapted to engage the rotatable structure and limit a degree of rotation of the rotatable structure. The rotation limiter may include a first flat surface of the bone plate and a first corresponding surface of the rotatable structure, the first flat surface and first corresponding surface configured to limit rotation of the rotatable structure beyond the locked orientation. The rotation limiter may include a second flat surface of the bone plate and a second corresponding surface of the rotatable structure, the second flat surface and second corresponding surface configured to limit rotation of the rotatable structure beyond an unlocked orientation. The degree of rotation is up to about 50 degrees. The bone plate may include a recess adapted to receive the rotatable structure; the recess may include a first flat surface adapted to engage a first corresponding surface of the rotatable structure to limit rotation of the rotatable structure beyond a locked orientation. The screw opening is configured to enable the screws to pivot within the screw opening within a range of motion ranging between approximately 45 degrees and approximately −45 degrees and where the head feature and lock feature are adapted to engage with each other with the screw pivoting within the range of motion and the rotatable structure in the locked orientation.

One general aspect includes an implant assembly. The implant assembly also includes a screw adapted to engage bone of a patient; the screw may include a head may include a head feature. The assembly also includes an implant adapted to receive the screw, the implant may include: a bone plate; and a rotatable structure coupled to the bone plate such that the rotatable structure is rotatable between a locked orientation and an unlocked orientation, the rotatable structure may include a bottom surface may include a lock feature adapted to engage the head feature when the rotatable structure is rotated to the locked orientation, thereby preventing rotation and back-out of the screw.

As used herein, "back-out" refers to a condition, state, position, and/or movement of a fastener from an initial position to a second position in which the fastener is less engaged and/or less connected to a corresponding part. The corresponding part can be a complementary part associated with the fastener or a part of a material that configured to receive the fastener. For example, where the fastener is a screw with external threads. Back-out can refer to the screw rotating in a reverse direction of the direction that tightens the screw with respect to internal threads or a material that receives the screw. In addition, back-out can include lateral or linear movement of a fastener out of a receiver, such as a hole, a nut, or the like. Back-out can be caused by a variety of forces, including but not limited to failure of threads of either the fastener or a hole having internal threads, a break in a shank of a fastener, a torque applied to the fastener in a direction opposite of the torque required to fasten the fastener to another part, or the like.

Implementations may include one or more of the following features. The implant assembly where the lock feature may include at least one groove and the head feature may include at least one ridge. The head feature may include a plurality of ridges, each ridge may include a long ramp and a short ramp, the long ramp adapted to facilitate sliding of the lock feature past one or more of the plurality of ridges as the rotatable structure rotates to the locked orientation. The lock feature may include a bump and the head feature may include a depression. The rotatable structure may include a bright color that facilitates connecting a driver to a drive feature of the rotatable structure, the drive feature adapted to receive torque from the driver to rotate the rotatable structure between the unlocked orientation and the locked orientation.

One general aspect includes a bone plate that may include: a recess bounded by a rim; and a pair of screw openings; a rotatable structure coupled to the bone plate such that the rotatable structure is rotatable, within the recess, between a locked orientation and an unlocked orientation, the rotatable structure may include: a pair of opposed arms, each of which is adapted to retain a screw positioned within one of the pair of screw openings when the rotatable structure is in the locked orientation, thereby restricting back-out of the screw; and a drive feature adapted to receive torque from a driver to rotate the rotatable structure between the locked orientation and the unlocked orientation. The implant also includes where the bone plate and the rotatable structure cooperate to define a detent mechanism adapted to retain the rotatable structure in the locked orientation, the detent mechanism may include: a niche defined in one of the rim and the rotatable structure; and an ear defined in the other of the rim and the rotatable structure, where the ear is sized to be received in the niche.

Implementations may include one or more of the following features. The vertebral implant where the detent mechanism is further adapted to retain the rotatable structure in an unlocked orientation. The niche is defined in a straight section of the rim and where the detent mechanism may include a second ear extending from the rotatable structure and where the second ear is sized to be received in the niche when the rotatable structure is in an unlocked orientation. The pair of opposed arms may include a plurality of radial grooves formed in a bottom surface of the rotatable structure and a corresponding plurality of ridges defined on a head of each screw positioned within each of the pair of screw openings. The pair of opposed arms extend in opposite directions from each other such that the pair of opposed arms engage two screws positioned within the pair of screw openings when the rotatable structure is in the locked orientation. The bone plate further may include a rotation limiter adapted to engage the rotatable structure and limit a degree of rotation of the rotatable structure when the rotatable structure is in the locked orientation. The bone plate may include three pairs of screw openings and the vertebral implant may include three rotatable structures, each rotatable structure positioned in the bone plate and adapted to retain a pair of screws, each screw positioned within a screw opening.

These and other features and advantages of the present disclosure will become more fully apparent from the following description and appended claims or may be learned by the practice of the disclosure as set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

Figure 1A:
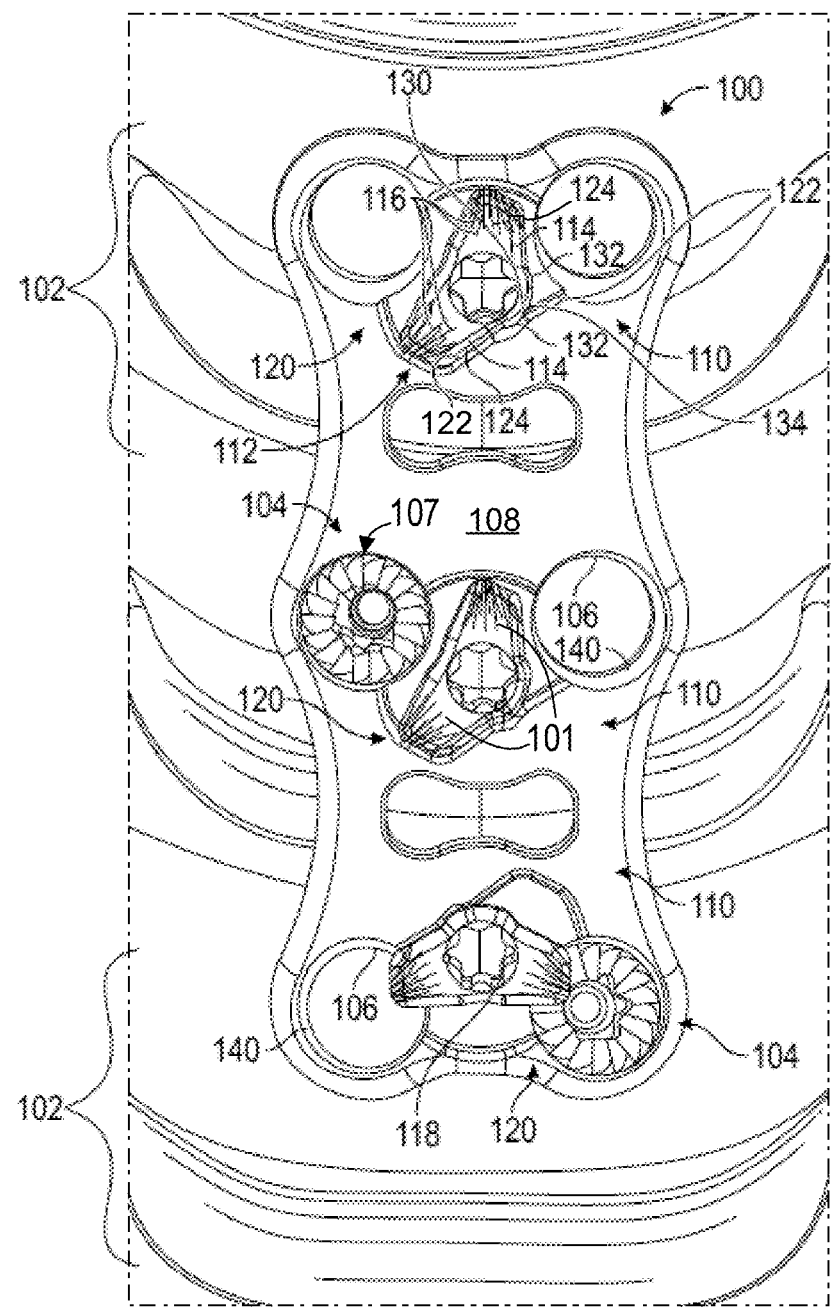
FIG. 1A is a perspective top view of implant assembly 100, according to one embodiment of the present disclosure.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application but is merely representative of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body.

A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The present disclosure provides an implant assembly that is affixed to one or more bones of a patient using one or more screws. In use, it is advantageous that the screws are prevented from backing out of the bone over time. The present disclosure provides a locking mechanism for this purpose.

In one embodiment, the present disclosure provides an implant assembly that comprises a cervical plate that is affixed to multiple vertebrae of the spine of a patient using a plurality of screws. Thus, one or more levels of the spine are immobilized. In use, it is advantageous that these screws are prevented from backing out of the cervical plate over time. The present disclosure provides a locking mechanism for this purpose.

For example, the implant assembly may have a thin profile for minimally invasive spine (MIS) surgery techniques which can reduce the size of the incisions, soft tissue damage, blood loss, less intrusive implants, post-operative pain, recovery time, risk of surgical complications, and the like. Furthermore, the shape, or profile, of an implant assembly can facilitate insertion of the implant during the surgery. A reliable locking mechanism can provide more stable and secure engagement between the implant and bones or vertebral bodies on either side of a space where the implant is positioned.

For example, using an implant assembly with a single rotatable structure that can secure two screws when in a locked orientation can result in a more reliable and effective expandable implant assembly. These and other unique features of the implant assembly are discussed below and illustrated in the accompanying drawings.

FIG. 1A illustrates an implant assembly 100. The implant assembly 100 may be secured to one or more adjacent bones 102 via one or more bone screws 104, which are inserted through screw openings 106 in the bone plate 108. In the example of FIG. 1A, the implant assembly 100 may include a bone plate 108 for a cervical spine.

A bone screw 104 is a type of screw adapted for use with implants in, on, or in connection with, parts of the body of a patient. As used herein, a "screw" refers to a type of fastener characterized by a helical ridge, known as a male thread (external thread). Screws may be made from a variety of materials including metal, plastic, composite materials, natural materials, or the like. Screws can be used to fasten materials by the engagement of the screw thread with a similar female thread (internal thread) in the matching part. Screws can also be self-threading (also known as self-tapping) where the thread cuts into the material when the screw is turned, creating an internal thread that helps pull fastened materials together and prevent pull-out. There are many screws for a variety of materials; those materials commonly fastened by screws include wood, sheet metal, and plastic. (Search "screw" on Wikipedia.com Apr. 6, 2021. Modified. Accessed Apr. 20, 2021.) A screw generally includes a head connected to a shank. The helical ridge extends from the shank.

As used herein, a "bone plate" refers to a flat structure. In certain embodiments, a bone plate can be configured to support a load (including a tension, compression, shear, torsion, and/or bending load). In certain embodiments, a bone plate may comprise a generally planar structure. A bone plate can be a separate structure connected to, or integrated with, another structure. Alternatively, a bone plate can be connected to part of another structure. A bone plate can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. A bone plate can be made from a variety of materials including, metal, plastic, ceramic, wood, fiberglass, or the like. One bone plate may be distinguished from another based on where the plate is positioned within a structure, component, or apparatus.

As illustrated in FIG. 1A, a locking mechanism 110 of the present disclosure may be incorporated into an implant assembly 100. However, in alternative embodiments, a locking mechanism 110 according to the present disclosure may be incorporated into any of a wide variety of implants, including but not limited to bone plates, spacers, fusion cages, arthroplasty implants, intramedullary implants, and the like. The locking mechanism 110 may be used to keep the bone screws 104 in their proper positions relative to the bones 102, overcoming the tendency of the bone screws 104 to loosen and withdraw from the bones 102 over time.

As embodied in FIG. 1A, the locking mechanism 110 may include a rotatable structure 112 with an unlocked orientation, in which the bone screws 104 are insertable into and/or withdrawable from the bones 102, and a locked orientation, in which the rotatable structure 112 blocks withdrawal of the bone screws 104 from the bones 102. As used herein, "unlocked orientation" refers to a position, condition, state, or configuration of a first object, component, part, apparatus, system, or assembly relative to another object, component, part, apparatus, system, or assembly in which the first object, component, part, apparatus, system, or assembly either alone or in combination with others parts or components enables, facilitates, opens, and/or permits motion and/or operation of the another object, component, part, apparatus, system, or assembly.

As used herein, "locked orientation" refers to a position, condition, state, or configuration of a first object, component, part, apparatus, system, or assembly relative to another object, component, part, apparatus, system, or assembly in which the first object, component, part, apparatus, system, or assembly either alone or in combination with others parts or components prevents, limits, impedes, is in a fixed relationship to, or restricts motion and/or operation of the another object, component, part, apparatus, system, or assembly.

The rotatable structure 112 is coupled to the bone plate 108 such that the rotatable structure 112 is rotatable between a locked orientation and an unlocked orientation.

In FIG. 1A, the top two locking mechanisms 110 are shown in the unlocked orientation, while the bottom locking mechanism 110 is shown in the locked orientation. Each of the rotatable structures 112 may have a drive feature 118 or other torque-receiving feature that mates with a tool, such as driver (not shown) with a star-shaped head, to allow a surgeon to rotate the rotatable structure 112.

Optionally, each of the rotatable structures 112 may include a pair of opposed arms 114, with each arm blocking withdrawal of a respective screw 104 when the rotatable structure 112 is in the locked orientation. In some embodiments, a locking mechanism may be shaped to block withdrawal of one, three, or more screws rather than two. In such configurations (not shown), the locking mechanisms may have one, three, or more arms, with one arm for each screw 104 the locking mechanism is to retain. In some embodiments, the arms 114 may not only interfere with linear motion of the screws 104 out of the bones 102 but may also interfere with rotation of the screws 104 in a direction that would loosen their engagement with the bones 102 (for example, counterclockwise in the view of FIG. 1A).

Figure 1B:
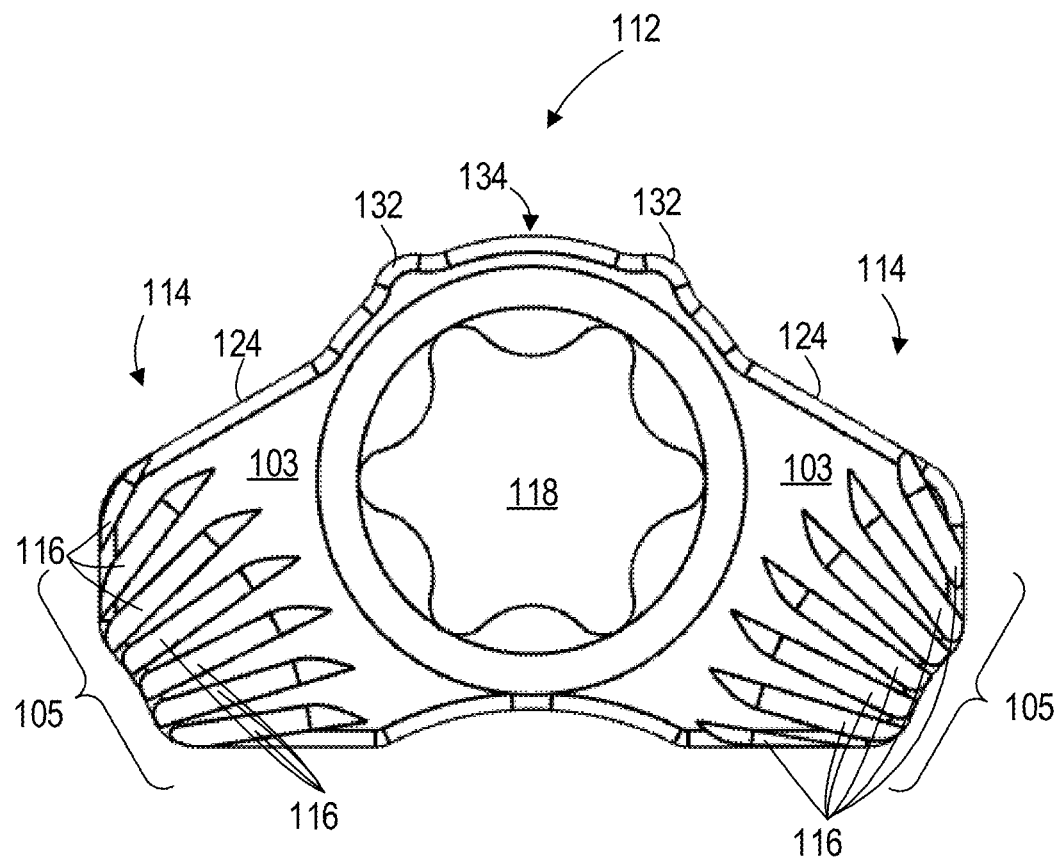
FIG. 1B is a bottom view of a rotatable structure 112, according to one embodiment of the present disclosure.

FIG. 1B is a bottom view of a rotatable structure 112, according to one embodiment of the present disclosure. The rotatable structure 112 may include a top surface 101 (See FIG. 1A) and a bottom surface 103. The bottom surface 103 may face the bone plate 108.

The bottom surface 103 includes a lock feature 105 configured to cooperate with a head feature 107 (See FIG. 1A, 2A) of a screw 104. As used herein, "feature" refers to a distinctive attribute or aspect of something. (Search "feature" on google.com. copyright Oxford Languages, 2021. Web. 20 Apr. 2021.) A feature may include a modifier that identifies a particular function or operation and/or a particular structure relating to the feature. For example, a lock feature 105 refers to a feature that relates to, or is involved in, a locking function. Similarly, head feature 107 refers to a feature that is associated with a particular part, such as a head of a screw 104.

In one embodiment, the lock feature 105 and head feature 107 include structures that cooperate to selectively engage and lock two structure relative to each other. For example, a lock feature 105 may include one or more radial grooves 116. And a head feature 107 may include one or more raised ridges 216 adapted to engage a corresponding one or more radial grooves 116 of the lock feature 105. Of course, in another embodiment, the lock feature 105 may include one or more raised ridges 216 and the head feature 107 may include a corresponding one or more radial grooves 116.

The lock feature 105 and head feature 107 are configured such that once they engage with each other they cooperate to prevent both counterclockwise rotation and linear backing out of each of the screws 104, relative to the bones 102. Having the lock feature 105 on the bottom surface 103 enables the rotatable structure 112 to engage the lock feature 105 with the head feature 107 when the rotatable structure 112 is in the locked orientation. By rotating the rotatable structure 112 to the locked orientation the lock feature 105 engages with the head feature 107 and this restricts rotation of a screw 104 within a screw opening 106.

In the illustrated embodiment, the lock feature 105 includes radial grooves 116. In embodiments for which the lock feature 105 includes radial grooves 116, the head feature 107 may include raised ridges 216 that correspond to the radial grooves 116. The raised ridges 216 of the head feature 107 may be shaped similarly to engage with the radial grooves 116.

In one embodiment, the radial grooves 116 extend like radii of a circle that can be centered approximately where a screw 104 may seat within a screw opening 106 of the bone plate 108. In another embodiment, the lock feature 105 may include a single groove 116 positioned along the bottom surface 103 of the arm 114. Similarly, the head feature 107 may include a single raised ridge 216 configured to engage a corresponding single radial groove 116 of the lock feature 105.

The rotatable structure 112 is positioned on the bone plate 108 such that the lock feature 105 is disengaged from the head feature 107 when the rotatable structure 112 is rotated to an unlocked orientation. Accordingly, the screw 104 can rotate within the screw opening 106. When the rotatable structure 112 is rotated to a locked orientation the lock feature 105 engages the head feature 107 and in this manner restricts rotation of the screw 104 within the screw opening 106.

Those of skill in the art will appreciate that the lock feature 105 and head feature 107 can be any structure on either the rotatable structure 112 and/or the head 210 configured and designed to engage with each other to accomplish the same result as the radial grooves 116 and raised ridges 216 described in the example embodiments herein. For example, in one embodiment, the lock feature 105 may be a bump or protuberance and the head feature 107 may be a depression or recess or hole such that these two features are configured to engage with each other to retain a screw 104 in the screw opening 106. In certain embodiments, the lock feature 105 and the head feature 107 may together be consider a type of detent mechanism.

Referring now to FIGS. 1A and 1B, each of the locking mechanisms 110 may further have a detent mechanism that tends to urge its rotatable structure 112 to move fully into the unlocked orientation or the locked orientation. As used herein, a "detent" refers to an apparatus, instrument, structure, device, component, feature, system, mechanism, assembly, or module structured, organized, configured, designed, arranged, or engineered to resist or arrest the motion or rotation of a wheel, axle, spindle, or other structure. (Search 'detent' on Wikipedia.com Jun. 22, 2020. Modified. Accessed Mar. 19, 2021.) In certain embodiments, the detent continues to resist or arrest the motion or rotation while in an engaged configuration and permits the motion or rotation when in a disengaged configuration. Examples of a detent may include a single structure or a combination of structures cooperating to serve as a detent. Examples of a detent and/or detent assembly include but are not limited to a ratchet and pawl, a nub or bump and a recess, a recess and a raised or extending structure, a notch and a pin, a set of notches or recesses in a smooth structure and a set of corresponding nubs, latches, pins, spring loaded ball bearings, or the like. In one embodiment, a detent may comprise an ear of a rotatable structure and a groove, niche, notch, or carve-out of another structure.

Specifically, each of the rotatable structures 112 may sit in a recess 120 manufactured into an outer surface of the bone plate 108. In one embodiment, the recess 120 may be a partially circular recess 120. Further, each of the partially circular recesses 120 may define a niche 130 that can receive either of two ears 132 protruding from a central hub 134 of the rotatable structure 112. One of the ears 132 may reside in the niche 130 in the locked orientation, and the other may reside in the niche 130 in the unlocked orientation. As the rotatable structure 112 approaches the locked orientation or the unlocked orientation, the corresponding ear 132 may slide into the niche 130, causing the rotatable structure 112 to "snap" into the locked configuration or the unlocked configuration. The engagement of an ear 132 within the niche 130 can provide either an audible "snap" as the two parts engage and/or the engaging ear 132 and niche 130 can provide a tactile movement that an operator can feel in a driver (not shown) that engages the drive feature 118 of the rotatable structure 112 to move the rotatable structure 112 into a locked orientation. Similarly, engagement of an ear 132 within the niche 130 can provide a tactile feedback to an operator using the driver to move the rotatable structure 112 into an unlocked orientation Thus, the niche 130 and the ears 132 may cooperate to define a detent mechanism as described above. Via such a detent mechanism, the surgeon may be sure the rotatable structure 112 has been fully rotated into the desired configuration. Further, the engagement of niche 130 and the ear 132 pertaining to the locked orientation may tend to retain the rotatable structure in the locked orientation, further ensuring that the rotatable structure 112 does not migrate to the unlocked orientation after the surgical procedure is complete.

Further, each of the locking mechanisms 110 may have a rotation limiter configured to engage the rotatable structure 112. The rotatable structure 112 limits a degree of rotation of the rotatable structure 112. The rotation limiter limits rotation of the rotatable structure 112 in either direction, beyond the locked orientation and the unlocked orientation, while allowing rotation of the rotatable structure 112 between the locked orientation and the unlocked orientation.

Rotation of each of the rotatable structures 112 may be limited by flat surfaces 122 manufactured into each of the partially circular recesses 120. Each of the flat surfaces 122 may engage a corresponding surface 124 associated with each of the arms 114 of the rotatable structure 112, thereby limiting the degree of rotation and deployment of each of the rotatable structures 112 beyond the unlocked and locked orientations. The corresponding surface 124 may be flat but does not have to be.

Thus, the flat surfaces 122 and the corresponding surfaces 124 may cooperate to define rotation limiters as described above. Notably, the rotatable structures 112 may rotate clockwise from the unlocked orientation into the locked orientation. Loosening rotation of the screws 104 (counter-clockwise) may tend to rotate the rotatable structures 112 further in the clockwise direction. Engagement of the flat surfaces 122 with the corresponding surfaces 124 may prevent such further clockwise rotation of the rotatable structures 112, thereby ensuring that the rotatable structures do not over-rotate clockwise, beyond the locked orientation, in response to torque tending to loosen the screws 104. Rather, as the rotatable structures 112 are unable to rotate further clockwise, counterclockwise (loosening) motion of the screws 104 may be prevented. Any counterclockwise torque in the screws 104 may tend to retain the rotatable structure 112 in the locked orientation, ensuring that the rotatable structure 112 does not migrate to the unlocked orientation after a surgical procedure is complete. This is more clearly shown and described in FIG. 3A.

The detent mechanism and the rotation limiter described above are only examples. It will be readily apparent to those of ordinary skill in the art that many other mechanisms may alternatively be used for guiding and/or limiting rotation of the rotatable structure 112. For example, in one embodiment, the rotatable structures 112 may not be seated in recesses. Rather, the flat surfaces 122 may protrude from the outer surface of the bone plate 108, as opposed to being disposed in the partially circular recesses 120 and may still provide the desired limitation on rotation. Detent mechanisms likewise need not be defined by a recess, but may, in some embodiments, be defined by protruding features and/or niches that are otherwise provided on the surface of the bone plate 108 and/or on the rotatable structures. Positioning the rotatable structures 112 in the partially circular recesses 120 as in FIG. 1A may help to reduce the profile of the locking mechanisms 110, helping the locking mechanisms 110 avoid damage to surrounding soft tissues or discomfort to a patient.

Figure 1C:
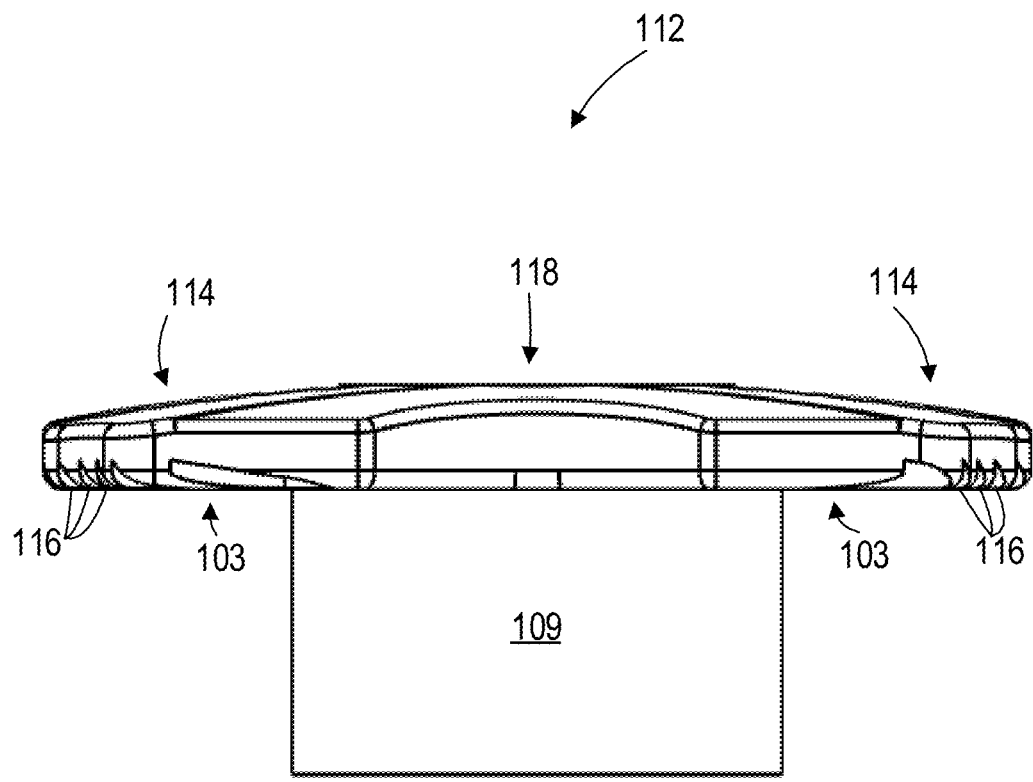
FIG. 1C is a front view of a rotatable structure 112, according to one embodiment of the present disclosure.

FIG. 1C is a front view of a rotatable structure 112, according to one embodiment of the present disclosure. The rotatable structure 112 includes a tube 109 that extends from the bottom surface 103. The tube 109 may be cylindrical and have a circular cross section. The tube 109 may serve to couple the rotatable structure 112 to the bone plate 108. In one embodiment, the rotatable structure 112 engages the bone plate 108 through a hole sized to accept a tube of the rotatable structure 112. In one embodiment, the tube 109 fits through the hole in the bone plate 108 in a slip fit. After the tube 109 is slip fit through the hole in the bone plate 108, the open, disconnected, end of the tube 109 may be swaged to flare the open-end outward such that the flared-out portion of the tube 109 engages the hole in the bone plate 108 and thereby retains the rotatable structure 112 within the hole.

A wide variety of screws may be used in conjunction with a locking mechanism 110 as shown in FIG. 1A. In some examples, the screws 104 may be designed for use in osteoporotic bone, for example, for aging patients. FIGS. 2A, 2B, 2C and 2D are a perspective view, a front elevation view, a front/side elevation section view, and a top view, respectively, of the exemplary screw 104 of FIG. 1A.

Figures 2A, 2B:
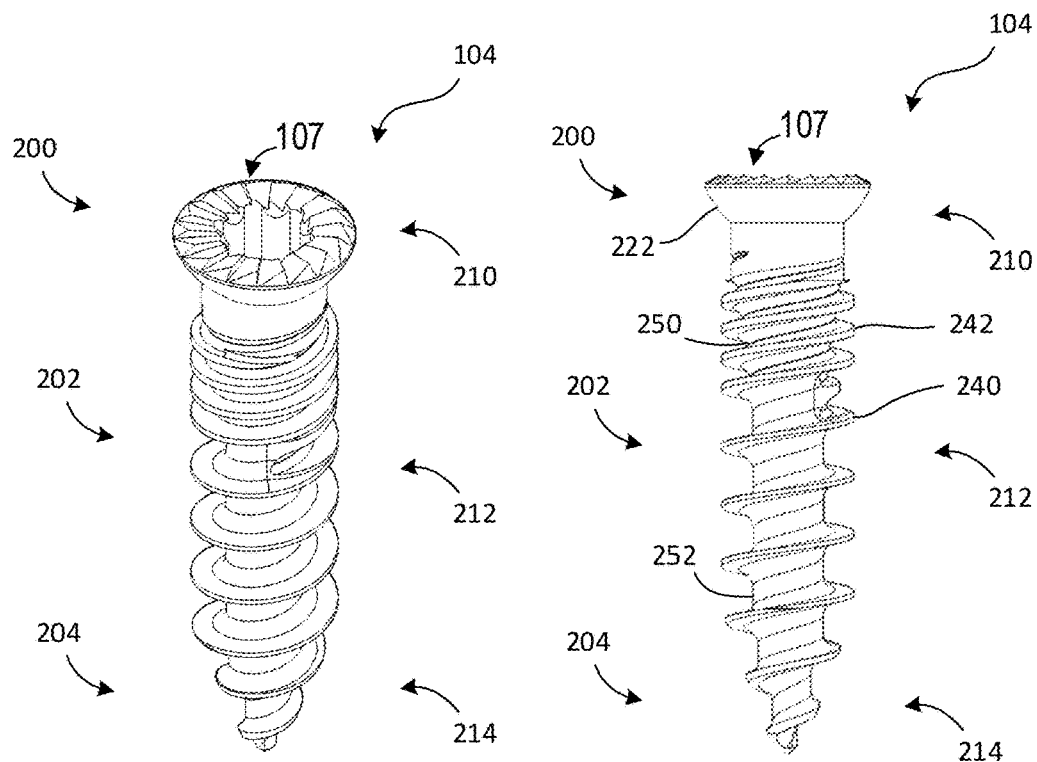
FIGS. 2A-D are a perspective view, a front elevation view, a front/side elevation section view, and a top view, respectively, of an exemplary screw 104 of FIG. 1A.
Figures 2C, 2D:
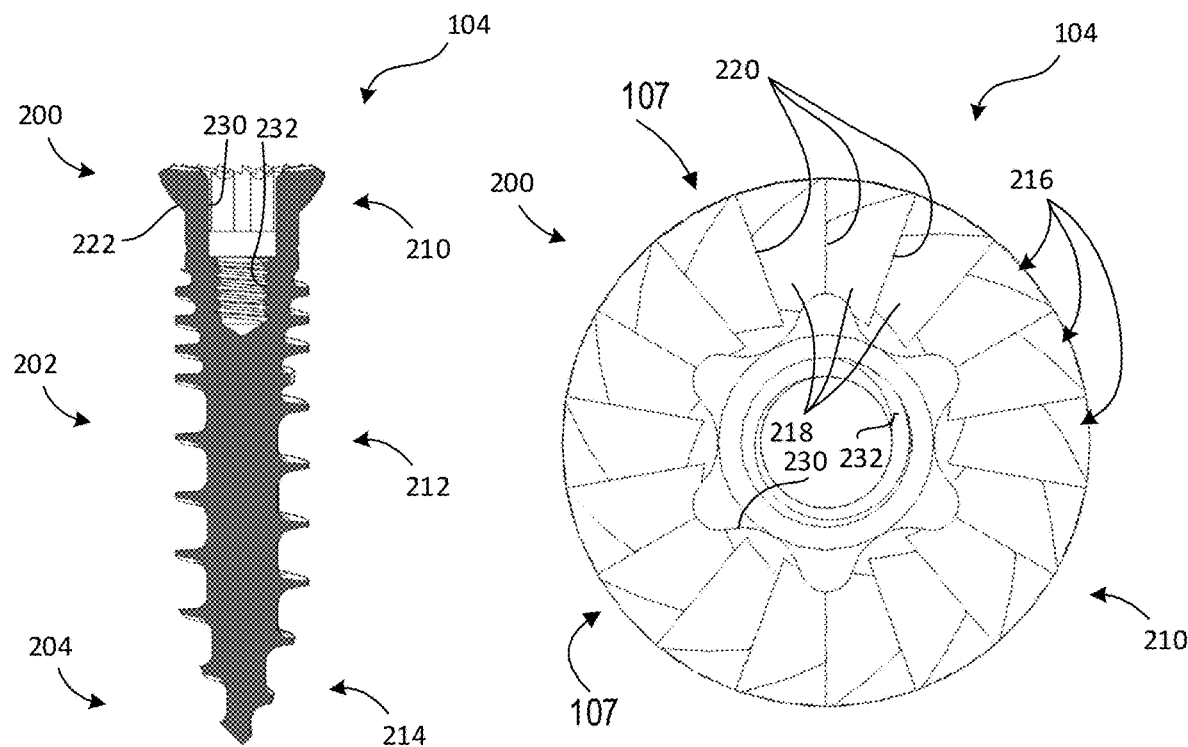

As shown in FIGS. 2A, 2B, and 2C, the screw 104 may have a proximal end 200, a distal end 204, and an intermediate portion 202 between the proximal end 200 and the distal end 204. The head 210 of the screw 104 may be at the proximal end 200, and the distal end 204 may terminate in a tip 214. A shank 212 may extend from the head 210 to the tip 214.

The head 210 may have the raised ridges 216 with sloping faces 218 and engagement faces 220, as described previously. Further, the head 210 may have additional features that optionally facilitate insertion of the screw 104 into the corresponding bone 102 and/or withdrawal of the screw 104 from the bone 102 (for example, as part of a revision procedure).

Specifically, the head 210 may have a socket 230 with a non-circular shape that engages a boss (not shown) on a driver with a corresponding male shape. As shown in FIG. 2D, the socket 230 may have a star shape with rounded points. Further, the head 210 may have a threaded socket 232 distal to the socket 230. The threaded socket 232 may receive a corresponding threaded boss (not shown) on a driver. In some embodiments, a driver (not shown) may have the boss and the threaded boss described above, so that the driver can mate with both the socket 230 and the threaded socket 232 for secure engagement with the head 210 of the screw 104, allowing the driver to advance or withdraw the screw 104.

The head 210 may be designed to work with a bone plate 108 by interfacing with the screw opening 106. For example, the head 210 may have a semispherical rim 222 that can engage a semispherical seat 140 of the screw opening 106. The semispherical rim 222 and the semispherical seat 140 may have similar or the same radii of curvature so that the semispherical rim 222 can reside in the semispherical seat 140 in any of a variety of relative orientations, about all three orthogonal axes.

The shank 212 may optionally have multiple screw threads. For example, a first screw thread 240 may extend from the head 210 to the tip 214. The first screw thread 240 may be designed to penetrate both cortical and cancellous bone. A second screw thread 242 may extend from the head 210 to the intermediate portion 202 of the screw 104, between the head 210 and the tip 214. In some embodiments, the second screw thread 242 may extend along a length of the shank 212 that generally corresponds to the expected thickness of cortical bone in the bone 102. Thus, the denser and stronger cortical portion of the bone 102 is penetrated by both the first screw thread 240 and the second screw thread 242, while the weaker and more porous cancellous portion of the bone 102 receives only the first screw thread. Such a design may maximize purchase in the cortical portion of the bone, while avoiding exertion of too much shear stress on the cancellous bone.

The first screw thread 240 and the second screw thread 242 may each have any known thread form. For example, the first screw thread 240 and the second screw thread 242 may be buttress threads, standard threads, square threads, and/or ACME threads, or may have any other thread shape known in the orthopedic field.

As further shown in FIGS. 2B and 2C, the first screw thread 240 and the second screw thread 242 may each have a substantially constant major diameter and pitch. Where it is present, the second screw thread 242 may be spaced such that its threads bisect the space between adjacent threads of the first screw thread 240. In some embodiments, the first screw thread 240 and the second screw thread 242 may have tapered minor diameter 250 that is smaller at the intermediate portion 202 than near the head 210. This tapered minor diameter may compress the cortical portion of the bone 102 for maximum purchase in the cortical bone as the screw 104 is inserted. The first screw thread 240, distally of the second screw thread 242, may have a constant minor diameter 252 that preserves and reduces stress on the cancellous portion of the bone 102.

FIG. 2D illustrates details of a head feature 107 of the screw 104. The raised ridges 216 on the head 210 of each of the screws 104 may have sloping faces 218 that slope toward the distal end 204 of the screw 104, along the clockwise direction. The sloping faces 218 may be connected by engagement faces 220 that are parallel to or more nearly parallel to the axis of the screw 104. Thus, the raised ridges 216 may be readily driven clockwise into the bone with a driver (not shown) with mating engagement ridges that engage the engagement faces 220. Such a mating interface may not generally be suitable for rotating the screw 104 counterclockwise, as the engagement ridges may slide along the sloping faces rather than transmitting counterclockwise torque. Thus, the raised ridges 216 may present an interface that facilitates driving the screws 104 into the bones 102 and keeping them in place, but not withdrawal of the screws 104 from the bones.

The radial grooves 116 of each arm 114 may be similarly shaped to mate with the raised ridges 216 on the head 210 of the corresponding screw 104 such that the clockwise rotation of the screw 104 (corresponding to tightening of the screw 104 within the bone 102) is permitted, while counterclockwise rotation of the screw 104 (corresponding to loosening of the screw 104 within the bone 102) is not permitted while the rotatable structure 112 is in the locked orientation. Thus, the engagement of the arms 114 with the heads 210 of the screws 104 may prevent the screws 104 from rotating in a manner that would loosen them relative to the bones 102 in which they reside.

Figure 3A:
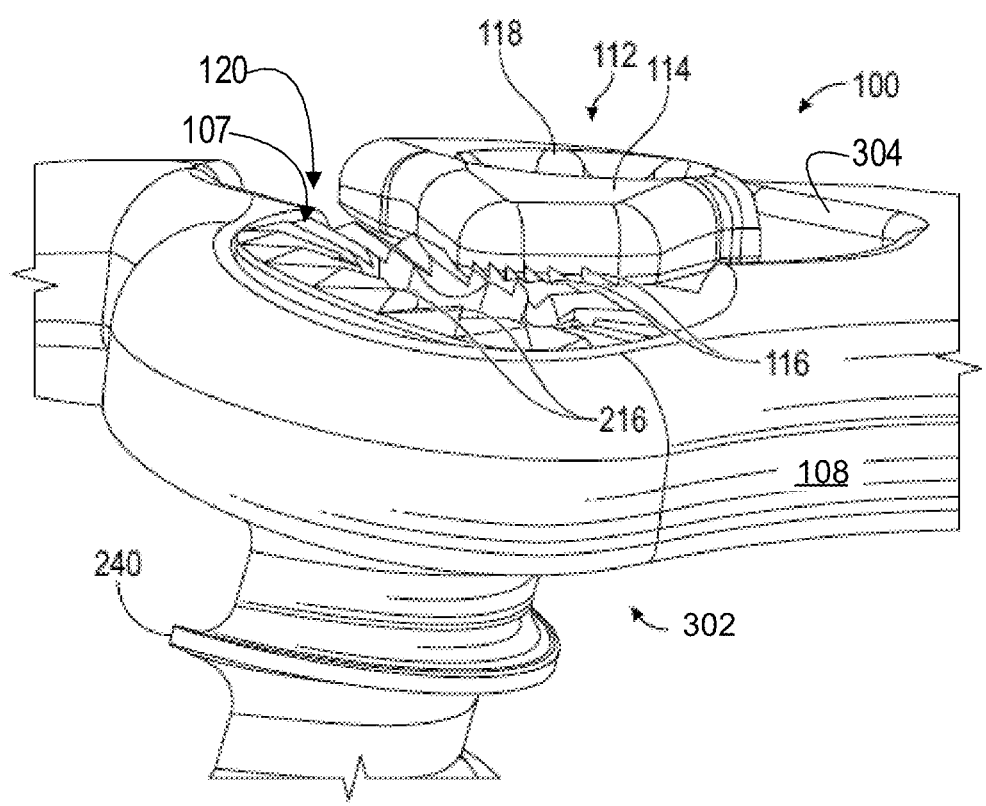
FIG. 3A-D are perspective side views of a rotatable structure 112 and exemplary screw 302, according to one embodiment of the present disclosure.

FIG. 3A depicts the implant assembly 100 of FIG. 1A, in use with a screw 302 according to an alternative configuration. The screw 302 has only a single thread start and may be more suitable than the screw 104 for use in healthy bone than the screw 104. The screw 302 is otherwise configured similarly to the screw 104.

FIG. 3A illustrates details of a recess 120 of the bone plate 108. In one embodiment, the recess 120 includes a rim 304 that may partially surround the recess 120. In certain embodiments, the rim 304 may include a feature for a detent mechanism that includes a structure on the rim 304 and a structure of the rotatable structure 112. For example, as illustrated in FIG. 1, the rim 304 can include a niche 130 and the rotatable structure 112 can include an ear 132 configured to seat within the niche 130.

FIG. 3A also illustrates a way the radial grooves 116 of the rotatable structures 112 interlock with the raised ridges 216 on the heads 210 of the screws 104. In the locked orientation, the radial grooves 116 may be oriented generally parallel to the raised ridges 216 that they overlie, as more clearly shown in FIG. 1A.

In one embodiment, the screw opening 106 includes a semispherical seat 140 (FIG. 1) that can engage a semispherical rim 222 of the head 210. The semispherical rim 222 and the semispherical seat 140 may have similar or the same radii of curvature so that the semispherical rim 222 can reside in the semispherical seat 140 in any of a variety of relative orientations, about all three orthogonal axes.

As shown, the raised ridges 216 may be more spaced apart than the radial grooves 116. Thus, the rotatable structure 112, in the locked orientation, may interlock with the head 210 of the screw 302 reliably, despite minor variations in the exact orientation of the head 210. There may be, for example, two of the radial grooves 116 for each of the raised ridges 216 overlied by the radial grooves 116.

Thus, the counterclockwise (loosening) rotation of the screw 302 may be limited to, at maximum, an angular displacement equal to half the angular width of the sector occupied by a single raised ridge 216 of the head 210. This amount of counterclockwise rotation of the screw 302 may be sufficient to cause the raised ridges 216 to engage the radial grooves 116, regardless of whether the raised ridges 216 were aligned with the radial grooves 116 as loosening began to occur. Any additional counterclockwise rotation may be blocked, as it would urge clockwise rotation of the rotatable structure 112, which cannot occur due to abutment of the corresponding surface 124 of the arm 114 with the flat surface 122 of the partially circular recess 120, as described above.

Figure 3B:
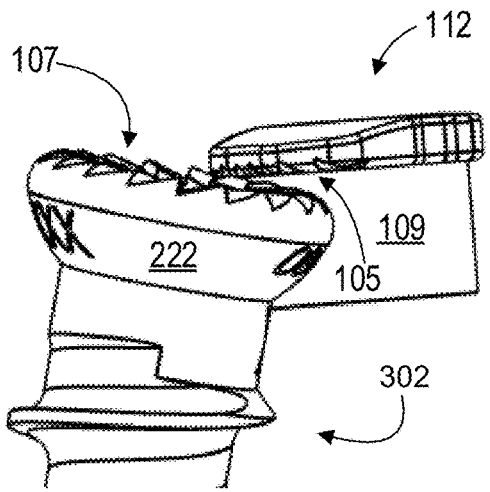
Figure 3C:
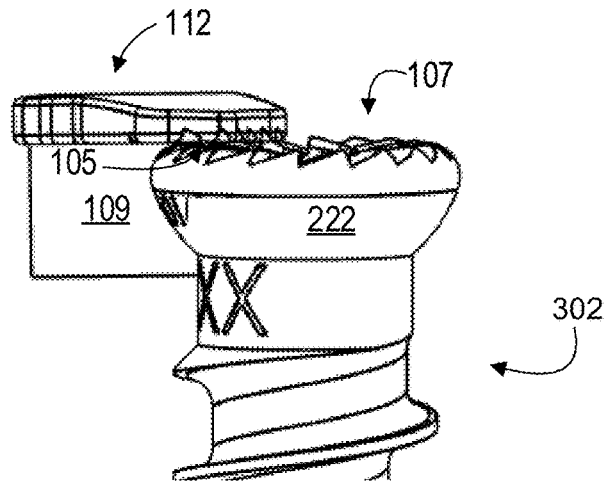
Figure 3D:
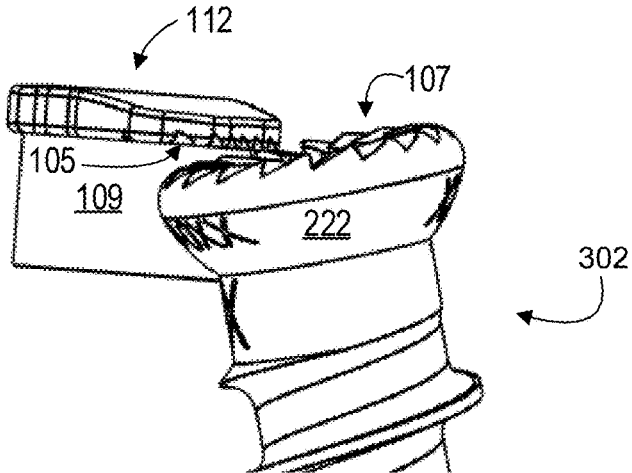

The semispherical seat 140 and semispherical rim 222 may cooperate to enable the screw 302 to pivot within the screw opening 106 within a range of motion. For example, the screw 302 may pivot within a range of motion ranging between approximately 45 degrees and approximately −45 degrees and the head feature 107 and lock feature 105 can engage and maintain engagement with each other with the rotatable structure 112 in a locked orientation. FIGS. 3B-3D illustrate examples of a screw 302 in three different orientations within the range of motion. FIG. 3B illustrates a screw 302 having its longitudinal axis oriented approximately 45 degrees from normal relative to the rotatable structure 112. FIG. 3C illustrates a screw 302 having its longitudinal axis oriented approximately 0 degrees from normal relative to the rotatable structure 112. FIG. 3D illustrates a screw 302 having its longitudinal axis oriented approximately −45 degrees from normal relative to the rotatable structure 112.

Figure 4A:
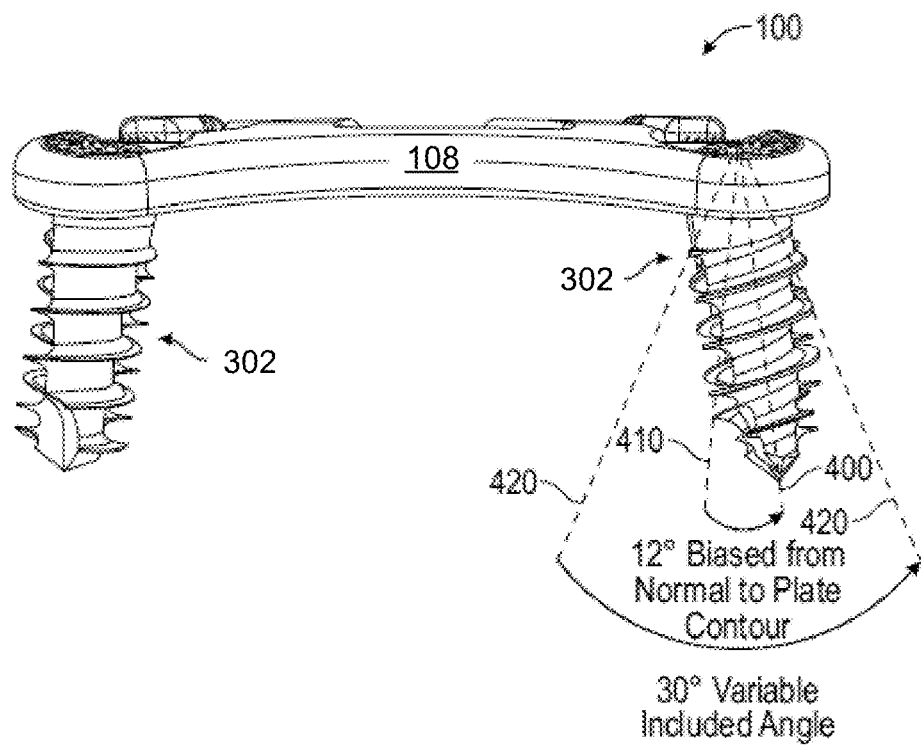
FIGS. 4A and 4B illustrate an implant assembly with four screws 302 inserted, according to one embodiment of the present disclosure.
Figure 4B:
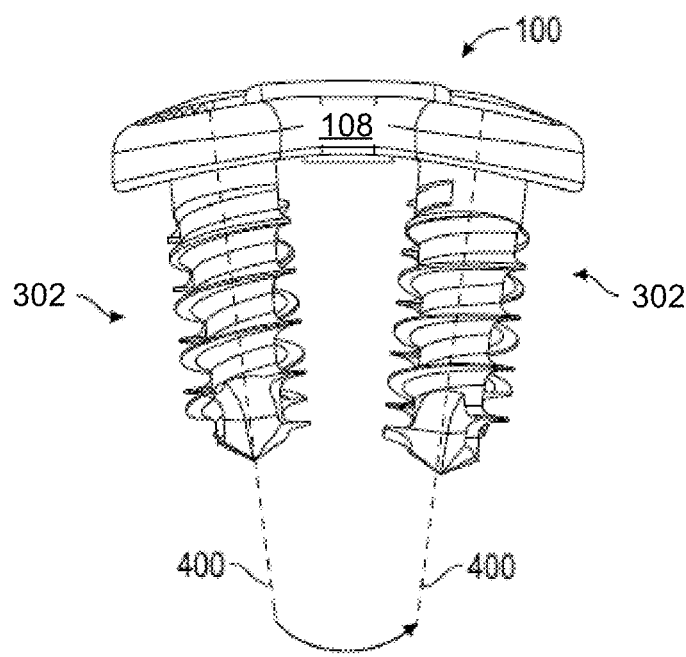

FIGS. 4A and 4B depict the implant assembly 100 with four of the screws 302 of FIG. 3A, inserted in a neutral orientation such that each of the screws 302 is at the center of its range of motion relative to the bone plate 108. As shown in FIG. 4A, each of the screws 302 may have a longitudinal axis 400 that extends generally away from the bone plate 108. In the neutral orientation shown, the longitudinal axis 400 may be oriented at about 12 degrees, within a coronal plane (parallel to the page of FIG. 4A) from a normal vector 410 extending from the nearest surface of the bone plate 108. This orientation is merely exemplary; in some embodiments, it may range from about −15 degrees to about 45 degrees, or more particularly, from about 0 degrees to about 30 degrees, or yet more particularly, from about 5 degrees to about 20 degrees.

Each of the screws 302 may be pivotable, relative to the bone plate 108, such that the longitudinal axis 400 has a range of motion 420 in all directions of approximately 30 degrees. This range of motion is merely exemplary; in some embodiments, the range of motion may range from about 5 degrees to about 55 degrees, or more particularly, from about 15 degrees to about 45 degrees, or yet more particularly, from about 25 degrees to about 35 degrees.

As shown in FIG. 4B, each of the screws 302 may have a "toe in," or angulation, within transverse plane (parallel to the page of FIG. 4B) relative to the screw 302 alongside it. This angulation may also be about 12 degrees. This angulation is merely exemplary; in some embodiments, it may range from about −15 degrees to about 45 degrees, or more particularly, from about 0 degrees to about 30 degrees, or yet more particularly, from about 5 degrees to about 20 degrees.

Figure 5:
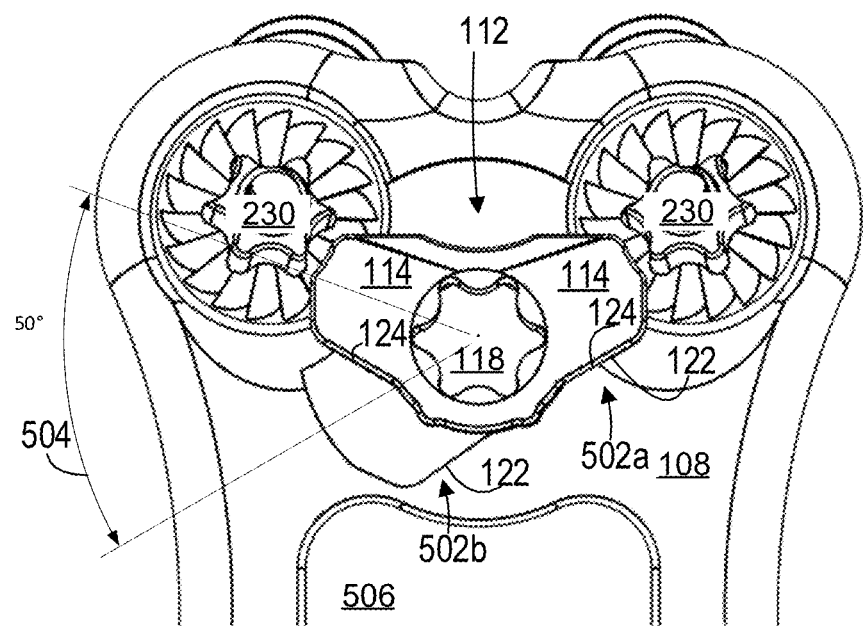
FIG. 5 is a perspective top view of part of an implant assembly 100, according to one embodiment of the present disclosure.

FIG. 5 is a perspective top view of part of an implant assembly 100, according to one embodiment of the present disclosure. FIG. 5 illustrates examples of a rotation limiter 502a, b that includes corresponding surface 122, 124. In one embodiment, a rotation limiter 502 limits rotation of the rotatable structure 112 in either, or both directions, beyond the locked orientation and the unlocked orientation, while allowing rotation of the rotatable structure 112 between the locked orientation and the unlocked orientation. For example, rotation limiter 502a may limit rotation of rotatable structure 112 beyond a locked orientation. Similarly, rotation limiter 502b may limit rotation of rotatable structure 112 beyond an unlocked orientation.

Rotation of the rotatable structures 112 may be limited by flat surfaces 122 manufactured into one or more partially circular recesses 120. Each of the flat surfaces 122 may engage a corresponding surface 124 associated with each of the arms 114 of the rotatable structure 112, thereby limiting the degree of rotation 504 and deployment of each of the rotatable structures 112 beyond the unlocked and locked orientations. The corresponding surface 124 may be flat but does not have to be.

In the illustrated example, the rotation limiter 502 can engage the rotatable structure 112 and thereby limit the degree of rotation 504. In one embodiment, the degree of rotation 504 can range between 0 degrees and about 50 degrees.

In certain embodiments, the rotatable structure 112 can be made from a variety of materials including plastic (e.g., ultra-high molecular weight polyethylene (UHMW). In such embodiments, a color for the rotatable structure 112 may be chosen to provide a high contrast between the rotatable structure 112 and other structures of the implant assembly 100 and/or parts of a patient's body. In one embodiment, the rotatable structure 112 may be made of a material having a bright color and/or a high contrast color such as yellow. Using a bright color (e.g., yellow) may be advantageous and facilitate a user connecting a driver (not shown) to a drive feature 118 of the rotatable structure 112. The drive feature 118 can receive torque from the driver to rotate the rotatable structure 112 between an unlocked orientation and a locked orientation and/or vice versa.

In certain embodiments, the implant assembly 100 may include a bone plate 108 having one or more openings 506. The opening 506 may serve as a window that permits a surgeon, post-operation, to view progress of a bone fusion procedure between bones 102 secured with the implant assembly 100. Alternatively, or in addition, the opening 506 can provide structural integrity to the bone plate 108. The openings 506 may mitigate coverage of body parts of a patient unnecessarily, may reduce the weight and amount of material used to form the bone plate 108, enable desirable flexing or stretching of the bone plate 108 as a patient moves. Alternatively, or in addition, the opening 506 may provide an aesthetic appeal for the bone plate 108.

Figure 6:
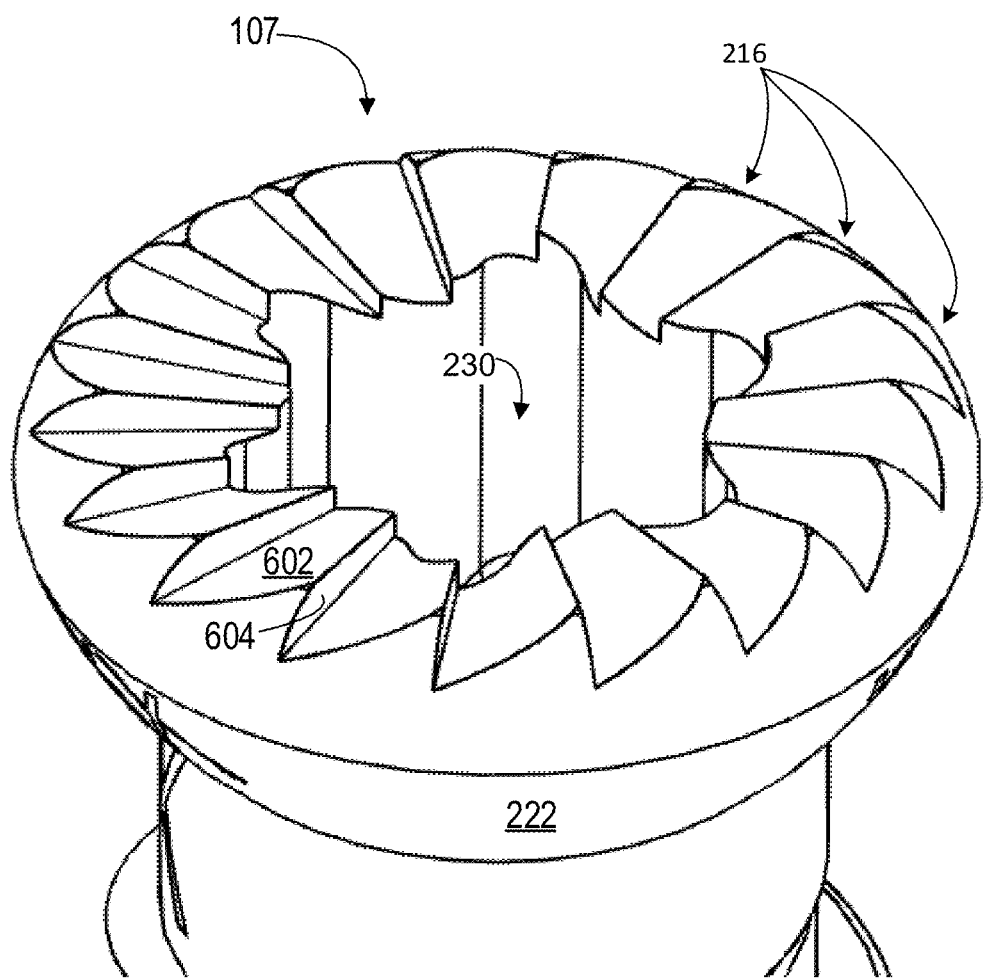
FIG. 6 is a perspective top view of an exemplary screw 104 of FIG. 1A, according to one embodiment of the present disclosure.

FIG. 6 is a perspective top view of an exemplary screw 104 of FIG. 1A, according to one embodiment of the present disclosure showing an enlarged version of the head feature 107. In particular, FIG. 6 shows a plurality of raised ridges 216. Looking at a single ridge 216, as one example, each ridge 216 may include a long ramp 602 and a short ramp 604. In one embodiment, the angle and size and relationship of the long ramp 602 and the short ramp 604 are designed, or selected, such that the long ramp 602 facilitates sliding of a lock feature 105 past one or more of the raised ridges 216 as a rotatable structure 112 is rotated to the locked orientation.

Figure 7:
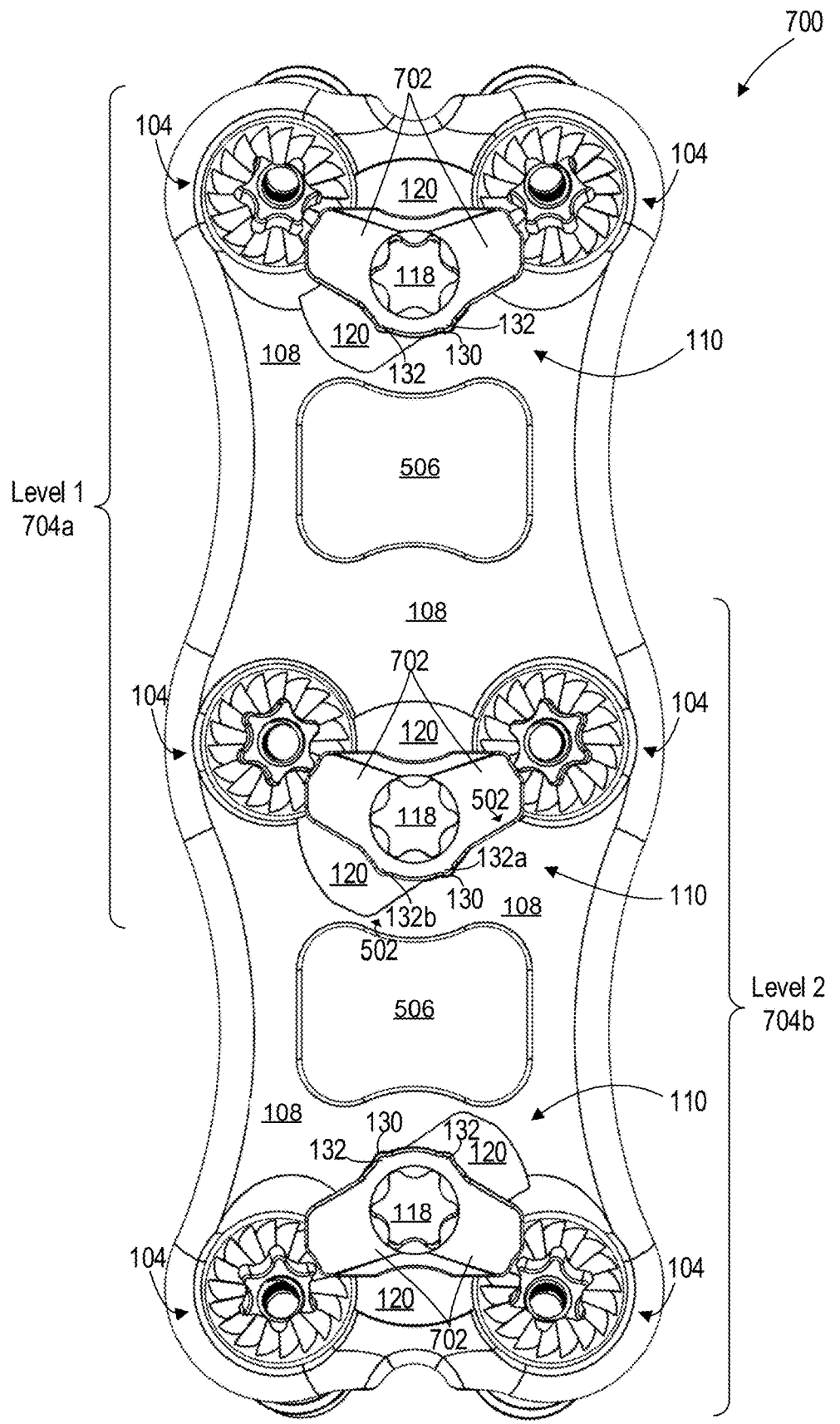
FIG. 7 is a top view of an implant assembly 700, according to one embodiment of the present disclosure.

FIG. 7 is a top view of an implant assembly 700, according to one embodiment of the present disclosure. The implant assembly 100 can include three pairs of screws 104 inserted within corresponding pairs of screw openings 106. Of course, in other implementations, each screw opening 106 may not include a screw 104. The implant assembly 100 includes three rotatable structures 112 that are each coupled to the bone plate 108 and that each include a pair of opposed arms 702.

In one embodiment, the pair of opposed arms 702 extend in opposite directions from each other. In one embodiment, the pair of opposed arms 702 may be in the shape of a delta shape, like a delta wing. In this manner, given the placement and orientation of the recess 120, rotatable structure 112, and the screw opening(s) 106, a single pair of opposed arms 702 can engage two screws 104 positioned within a pair of screw openings 106 when the rotatable structure 112 is in a locked orientation. The arm 114 serves to restrict back-out of the screw 104. The rotatable structures 112 also include a drive feature 118 that can receive torque from a driver to rotate the rotatable structure 112 between the locked orientation and an unlocked orientation.

Together the bone plate 108 and rotatable structure 112 can cooperate to create a detent mechanism. The detent mechanism can retain the rotatable structure 112 in a locked orientation and may include a niche 130 and at least one ear 132. In the illustrated embodiment, the detent mechanism can include a niche 130 and one or more ears 132. The niche 130 and/or ears 132 can be formed in either the rotatable structure 112 (e.g., along an edge of the rotatable structure 112) and/or in the bone plate 108, for example in a rim 304 of a recess 120.

In one embodiment, the bone plate 108 may include a single niche 130 for each rotatable structure 112. The niche 130 may be formed in a straight section of the rim 304 around the recess 120. The niche 130 may serve as part of a detent mechanism that secures two ears 132. For example, in one embodiment, a detent mechanism includes a niche 130 and two ears 132. A first ear 132a that fits within the niche 130 when the rotatable structure 112 is in the locked orientation and a second ear 132b and that seats within the same niche 130 when the rotatable structure 112 is in the unlocked orientation. (See FIG. 1) The second ear 132b and the first ear 132a may be sized to be received in the niche 130. The bone plate 108 may include one or more openings 506.

FIG. 7 illustrates one example of an implant assembly that can serve as a vertebral implant 700. In this example, the bone plate 108 can include three pairs of screw openings 106 and the vertebral implant can include three rotatable structures 112. Each rotatable structure 112 may be positioned in, or on, the bone plate 108 and adapted to retain a pair of screws 104. Each screw 104 is positioned within a screw opening 106 of the three pairs of screw openings 106.

In one embodiment, a vertebral implant 700 may be configured, designed, engineered, or adapted to support one or more levels 704. In such an embodiment, the bone plate 108 may be sized to support the one or more levels 704. As used herein, a "level" refers to a location within the body of a patient that includes a bone on either end of the level with another body part of section between the bones 102. For example, the vertebral implant 700 can be used to secure adjacent vertebral bodies that may include either a cervical disc, a cervical fixation implant, or a combination of all, or part of, a cervical disc and a cervical fixation implant in between each vertebral body.

FIG. 7 illustrates an embodiment of a vertebral implant 700 that may include two levels 704a, 704b. Each level 704 can include one or more screw openings 106 that receive corresponding screws 104 and one or more locking mechanisms 110 that can include corresponding rotatable structures 112. In one embodiment, each level 704 can include a pair of screw openings 106 that receive corresponding pair of screws 104 and two locking mechanisms 110 that can include corresponding rotatable structures 112. In certain embodiments of the implant assembly 100, the opening 506 may serve as a window that permits a surgeon or other user to view a condition of parts between bones 102 secured with the vertebral implant 700 installed.

Each level 704 can include one or more locking mechanisms 110. Adjacent levels (e.g., level 704a and level 704b) can share a common locking mechanism 110 between them. Those of skill in the art recognize that the present disclosure supports embodiments of an implant assembly 100 that supports any number of levels 704. For each number of levels, the implant assembly 100 may include one more pair of screw openings 106, corresponding pair of screws 104, and locking mechanism 110 or rotatable structure 112 than the number of levels. For a example, an implant assembly 100 that support two levels may include three rotatable structures 112, three pairs of screw openings 106, and three corresponding pair of screws 104. Likewise, an implant assembly 100 that supports one level may include two rotatable structures 112, two pairs of screw openings 106, and two corresponding pair of screws 104. In certain embodiments, the implant assembly 100 may include a bone plate 108, a rotatable structure 112, a pair of screw openings 106 and screws may not be included in the implant assembly 100.

Those of skill in the art will appreciate that the presented disclosure supports an embodiment of an implant assembly 100 that supports no levels 704. Such an embodiment may include one or more screw openings 106, one or more screws 104, and at least one locking mechanism 110 that may include at least one rotatable structure 112.

Figure 8:
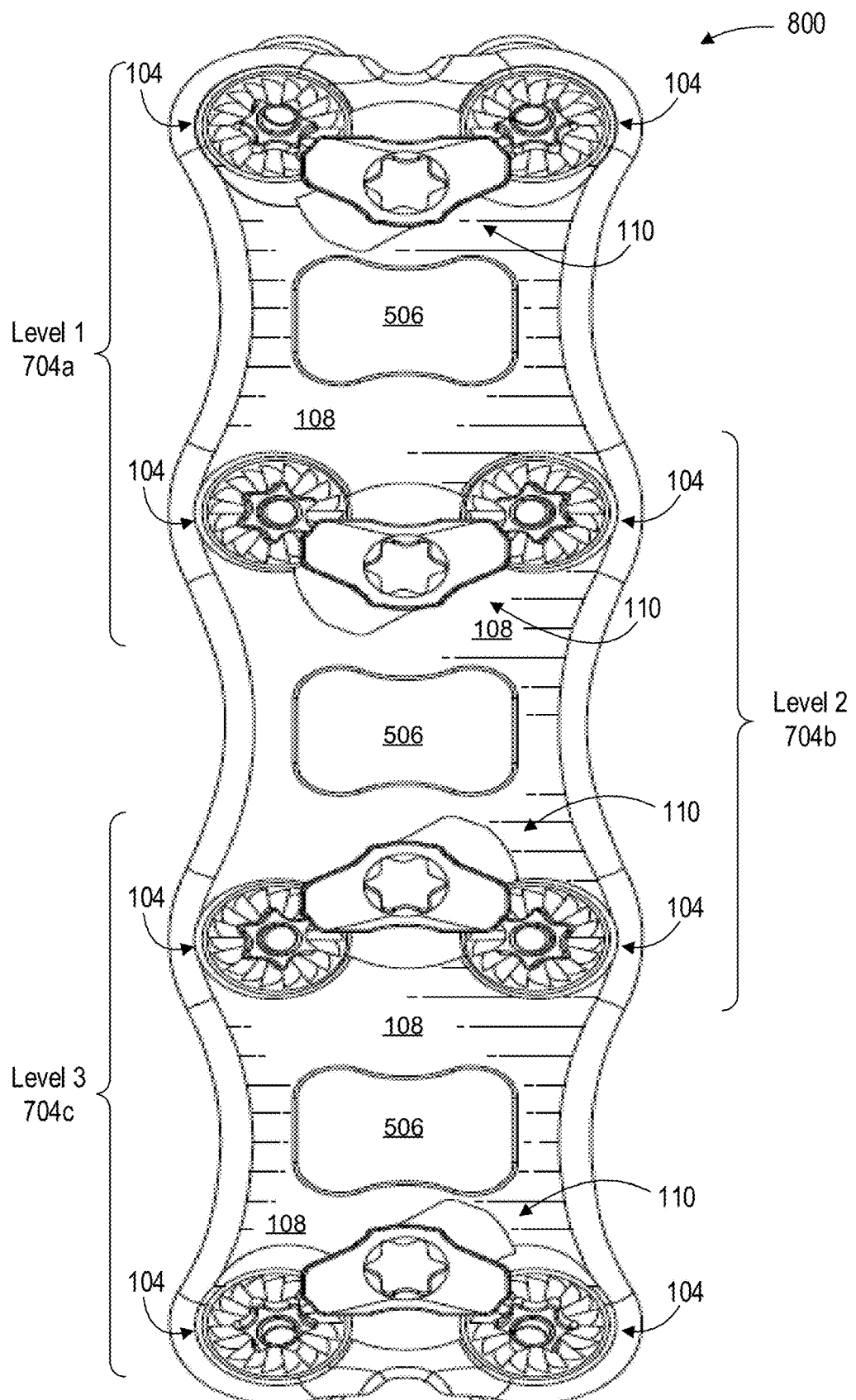
FIG. 8 is a top view of an implant assembly 800, according to one embodiment of the present disclosure.

FIG. 8 is a top view of an implant assembly 800, according to one embodiment of the present disclosure. The implant assembly 800 may serve as a vertebral assembly. In the illustrated embodiment, the implant assembly 800 supports three levels 704 (e.g., level 704a, level 704b, and level 704c). The present disclosure supports move levels 704 as well. In one embodiment, the implant assembly 100 can support 5 levels and may include four rotatable structures 112, four pairs of screw openings 106, and four corresponding pair of screws 104.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. An implant assembly comprising:
   a screw comprising a head comprising a head feature comprising one of a ridge and a radial groove; and an implant securable to a bone of a patient with the screw, the implant comprising:
  a bone plate comprising a screw opening sized to receive the screw; and
  a rotatable structure coupled to the bone plate such that the rotatable structure is rotatable between a locked orientation and an unlocked orientation, the rotatable structure comprising:
    a top surface;
    a bottom surface comprising a lock feature comprising the other of the ridge and the radial groove;
  wherein the lock feature is positioned such that:
    with the rotatable structure in the locked orientation, the lock feature engages the head feature, thereby restricting rotation of the screw within the screw opening; and
    with the rotatable structure in the unlocked orientation, the lock feature disengages from the head feature, thereby permitting rotation of the screw within the screw opening;
  wherein the screw opening is configured to enable the screw to pivot within the screw opening within a range of motion ranging between approximately 45 degrees and approximately −45 degrees and wherein the head feature and lock feature are adapted to engage with each other with the screw pivoting within the range of motion and the rotatable structure in the locked orientation.

2. The implant assembly of claim 1, wherein the lock feature comprises a plurality of radial grooves and the head feature comprises a plurality of ridges, the plurality of radial grooves adapted to engage the plurality of ridges.

3. The implant assembly of claim 1, further comprising a rotation limiter adapted to engage the rotatable structure and limit a degree of rotation of the rotatable structure.

4. The implant assembly of claim 3, wherein the rotation limiter comprises a first flat surface of the bone plate and a first corresponding surface of the rotatable structure, the first flat surface and first corresponding surface configured to limit rotation of the rotatable structure beyond the locked orientation.

5. The implant assembly of claim 4, wherein the rotation limiter comprises a second flat surface of the bone plate and a second corresponding surface of the rotatable structure, the second flat surface and second corresponding surface configured to limit rotation of the rotatable structure beyond the unlocked orientation.

6. The implant assembly of claim 3, wherein the degree of rotation is up to about 50 degrees.

7. The implant assembly of claim 1, wherein the bone plate comprises a recess adapted to receive the rotatable structure, the recess comprising a first flat surface adapted to engage a first corresponding surface of the rotatable structure to limit rotation of the rotatable structure beyond the locked orientation.

8. An implant assembly, comprising:
  a screw adapted to engage bone of a patient, the screw comprising a head comprising a head feature;
  an implant adapted to receive the screw, the implant comprising:
    a bone plate; and
    a rotatable structure coupled to the bone plate such that the rotatable structure is rotatable between a locked orientation and an unlocked orientation, the rotatable structure comprising a bottom surface comprising a lock feature adapted to engage the head feature when the rotatable structure is rotated to the locked orientation, thereby preventing rotation and back-out of the screw;
  wherein the head feature comprises a plurality of ridges, each ridge comprising a long ramp and a short ramp, the long ramp adapted to facilitate sliding of the lock feature past one or more of the plurality of ridges as the rotatable structure rotates to the locked orientation.

9. The implant assembly of claim 8, wherein the lock feature comprises at least one groove.

10. The implant assembly of claim 8, wherein the rotatable structure comprises a bright color that facilitates connecting a driver to a drive feature of the rotatable structure, the drive feature adapted to receive torque from the driver to rotate the rotatable structure between the unlocked orientation and the locked orientation.

11. An implant assembly comprising:
  a bone plate comprising:
    a recess bounded by a rim;
    a pair of screw openings; and
    a pair of screws;
  a rotatable structure coupled to the bone plate such that the rotatable structure is rotatable, within the recess, between a locked orientation and an unlocked orientation, the rotatable structure comprising:
    a pair of opposed arms, each of which is adapted to retain one of the pair of screws screws positioned within one of the pair of screw openings when the rotatable structure is in the locked orientation, thereby restricting back-out of the screw; and
    a drive feature adapted to receive torque from a driver to rotate the rotatable structure between the locked orientation and the unlocked orientation; and
  wherein the bone plate and the rotatable structure cooperate to define a detent mechanism adapted to retain the rotatable structure in the locked orientation, the detent mechanism comprising:
    a niche defined in one of the rim and the rotatable structure; and
    an ear defined in the other of the rim and the rotatable structure, wherein the ear is sized to be received in the niche;
  wherein the detent mechanism is further adapted to retain the rotatable structure in the unlocked orientation.

12. The implant assembly of claim 11, wherein the niche is defined in a straight section of the rim and wherein the detent mechanism comprises a second ear extending from the rotatable structure and wherein the second ear is sized to be received in the niche when the rotatable structure is in the unlocked orientation.

13. The implant assembly of claim 11, wherein the pair of opposed arms comprise a plurality of radial grooves formed in a bottom surface of the rotatable structure and a corresponding plurality of ridges defined on a head of each screw positioned within each opening of the pair of screw openings.

14. The implant assembly of claim 11, wherein the pair of opposed arms extend in opposite directions from each other such that the pair of opposed arms engage the pair of screws positioned within the pair of screw openings when the rotatable structure is in the locked orientation.

15. The implant assembly of claim 11, wherein the bone plate further comprises a rotation limiter adapted to engage the rotatable structure and limit a degree of rotation of the rotatable structure when the rotatable structure is in the locked orientation.

16. The implant assembly of claim 11, wherein the bone plate comprises three pairs of screw openings and the implant assembly further comprises two additional rotatable structures, each rotatable structure positioned in the bone plate and adapted to retain a pair of screws, each screw positioned within a screw opening.

17. An implant assembly comprising:
a bone plate comprising:
a recess bounded by a rim;
a pair of screw openings; and
a pair of screws;
a rotatable structure coupled to the bone plate such that the rotatable structure is rotatable, within the recess, between a locked orientation and an unlocked orientation, the rotatable structure comprising:
a pair of opposed arms, each of which is adapted to retain one of the pair of screws positioned within one of the pair of screw openings when the rotatable structure is in the locked orientation, thereby restricting back-out of the screw; and
a drive feature adapted to receive torque from a driver to rotate the rotatable structure between the locked orientation and the unlocked orientation; and
wherein the bone plate and the rotatable structure cooperate to define a detent mechanism adapted to retain the rotatable structure in the locked orientation, the detent mechanism comprising:
a niche defined in one of the rim and the rotatable structure; and
an ear defined in the other of the rim and the rotatable structure, wherein the ear is sized to be received in the niche;
wherein the niche is defined in a straight section of the rim and wherein the detent mechanism comprises a second ear extending from the rotatable structure and wherein the second ear is sized to be received in the niche when the rotatable structure is in the unlocked orientation.

18. The implant assembly of claim 17, wherein the detent mechanism is further adapted to retain the rotatable structure in the unlocked orientation.

19. The implant assembly of claim 17, wherein the pair of opposed arms comprise a plurality of radial grooves formed in a bottom surface of the rotatable structure and a corresponding plurality of ridges defined on a head of each screw positioned within each opening of the pair of screw openings.

20. The implant assembly of claim 17, wherein the pair of opposed arms extend in opposite directions from each other such that the pair of opposed arms engage the pairs of screws positioned within the pair of screw openings when the rotatable structure is in the locked orientation.

21. The implant assembly of claim 17, wherein the bone plate further comprises a rotation limiter adapted to engage the rotatable structure and limit a degree of rotation of the rotatable structure when the rotatable structure is in the locked orientation.

22. The implant assembly of claim 17, wherein the bone plate comprises three pairs of screw openings and the implant assembly further comprises two additional rotatable structures, each rotatable structure positioned in the bone plate and adapted to retain a pair of screws, each screw positioned within a screw opening.

* * * * *